United States Patent [19]

Tanaka et al.

[11] Patent Number: 5,693,826
[45] Date of Patent: Dec. 2, 1997

[54] PROCESS FOR THE PRODUCTION OF UNSATURATED PHOSPHONIC ESTER

[75] Inventors: Masato Tanaka; Li-Biao Han, both of Tsukuba, Japan

[73] Assignee: Director-General Of Agency Of Industrial Science And Technology, Japan

[21] Appl. No.: 699,391

[22] Filed: Aug. 19, 1996

[30] Foreign Application Priority Data

Sep. 14, 1995 [JP] Japan .................................. 7-237425

[51] Int. Cl.$^6$ .......................... C07D 333/06; C07E 7/02; C07E 9/09
[52] U.S. Cl. ................ 549/6; 556/404; 558/113
[58] Field of Search .................... 556/404; 558/113; 549/6

[56] References Cited

PUBLICATIONS

Tetrahedron Letters vol. 34, No. 52, pp. 8543–85434 1993.
J. Org. Chem., vol. 58, No. 13, pp. 3516–3520, 1993.
Synthesis, Issue 5, pp. 414–416, 1991.
J. Org. Chem., vol. 55, No. 5, 1513–16, 1990.
J. Org. Chem., vol. 51, No. 19, pp. 3572–3576, 1986.

*Primary Examiner*—José G. Dees
*Assistant Examiner*—Mary C. Cebulak
*Attorney, Agent, or Firm*—Lorusso & Loud

[57] ABSTRACT

An unsaturated phosphonic ester is produced by reaction of an acetylene compound with a secondary phosphite in the presence of a palladium complex catalyst.

2 Claims, No Drawings

PROCESS FOR THE PRODUCTION OF UNSATURATED PHOSPHONIC ESTER

BACKGROUND OF THE INVENTION

This invention relates to a process for the production of an unsaturated phosphonic ester.

Unsaturated phosphonic esters are useful in the fields of medicaments and agricultural chemicals as intermediate compounds for the production of physiologically active substances. One known method of producing a phosphonic ester is substitution of the corresponding unsaturated halogenated compound with a secondary phosphite in the presence of a base. The known method has a problem because a large amount of a salt of the base with HX (X represents a halogen atom) is formed. Additionally, the unsaturated halogenated compound is poisonous and is not easily commercially available.

SUMMARY OF THE INVENTION

In accordance with the present invention there is provided a process for the production of an unsaturated phosphonic ester expressed by the following formula:

$$R^1CH=C(R^2)PO(OR^3)_2$$

wherein $R^1$ and $R^2$ are independently selected from the group consisting of a hydrogen atom, an alkyl group, a cycloalkyl group, an aryl group, a heteroaryl group, an aralkyl group, an alkenyl group, an alkoxy group, an aryloxy group and a silyl group and $R^3$ is selected from the group consisting of an alkyl group, a cycloalkyl group, an aralkyl group and an aryl group. The process includes reacting an acetylene compound expressed by the following formula:

$$R^1C\equiv CR^2$$

wherein $R^1$ and $R^2$ are as defined above, with a secondary phosphite expressed by the following formula:

$$HPO(OR^3)_2$$

wherein $R^3$ is as defined above, in the presence of a palladium complex catalyst.

The present invention also provides a process for the production of an unsaturated phosphonic ester expressed by at least one of the following formulas:

$$R^4CH=C[PO(OR^3)_2]-R^5-C[PO(OR^3)_2]=CHR^6$$

$$R^4C[PO(OR^3)_2]=CH-R^5-CH=CR^6[PO(OR^3)_2]$$

wherein $R^3$ is selected from the group consisting of an alkyl group, a cycloalkyl group, an aralkyl group and an aryl group, $R^4$ and $R^6$ are independently selected from the group consisting of a hydrogen atom, an alkyl group, a cycloalkyl group, an aryl group, a heteroaryl group, an aralkyl group, an alkenyl group, an alkoxy group, an aryloxy group and a silyl group and $R^5$ is a divalent group selected from the group consisting of an alkylene group, a cycloalkylene group, an arylene group, a heteroarylene group, an aralkylene group, an alkenylene group, an alkylenedioxy group, an arylenedioxy group, an oxaalkylene group and an oxaalkylenearylene group. The process includes reacting an acetylene compound expressed by the following formula:

$$R^4C\equiv C-R^5-C\equiv CR^6$$

wherein $R^4$, $R^5$ and $R^6$ are as defined above, with a secondary phosphite expressed by the following formula:

$$HPO(OR^3)_2$$

wherein $R^3$ is as defined above, in the presence of a palladium complex catalyst.

It is an object of the present invention to provide a simply process which can devoid of the problems of the conventional process.

Another object of the present invention is to provide a process which can produce an unsaturated phosphonic ester with a high yield.

Other objects, features and advantages of the present invention will become apparent from the detailed description of the preferred embodiments to follow.

DETAILED DESCRIPTION OF THE PREFERRED EMBODIMENTS OF THE INVENTION

The secondary phosphite used in the process of the present invention is represented by the formula $HPO(OR^3)_2$. Examples of suitable group $R^3$ include a methyl group, an ethyl group, a hexyl group, a cyclohexyl group, a phenyl group and a benzyl group.

The acetylene compound used in the process of the present invention is represented by the formula $R^1C\equiv CR^2$ or $R^4C\equiv C-R^5-C\equiv CR^6$. The groups $R^1$, $R^2$, $R^4$ and $R^6$ are independently selected from the group consisting of a hydrogen atom, an alkyl group, a substituted alkyl group, a cycloalkyl group, a substituted cycloalkyl group, an aryl group, a substituted aryl group, a heteroaryl group, a substituted heteroaryl group, an aralkyl group, a substituted aralkyl group, an alkenyl group, a substituted alkenyl group, an alkoxy group, a substituted alkoxy group, an aryloxy group, a substituted aryloxy group, a silyl group and a substituted silyl group. Examples of suitable groups $R^1$, $R^2$, $R^4$ and $R^6$ include a hydrogen atom, a methyl group, a propyl group, a benzyl group, a phenyl group, a thienyl group, a 3-butenyl group, an ethoxy group, a phenoxy group and a trimethlsilyl group. The group $R^5$ is a divalent group selected from the group consisting of an alkylene group, a substituted alkylene group, a cycloalkylene group, a substituted cycloalkylene group, an arylene group, a substituted arylene group, a heteroarylene group, a substituted heteroarylene group, an aralkylene group, a substituted aralkylene group, an alkenylene group, a substituted alkenylene group, an alkylenedioxy group, a substituted alkylenedioxy group, an arylenedioxy group, a substituted arylenedioxy group, an oxalkylene group, a substituted oxalkylene group, an oxalkylenearylene group and a substituted oxalkylenearylene group. Examples of suitable group $R^5$ includes a tetramethylene group, a phenylene group, a thienylene group, a ferrocenylene group and a phenylenedioxy group. Illustrative of suitable acetylene compounds are acetylene, butyne, octyne, phenylacetylene, trimethylsilylacetylene, ethynylthiophene, diethynylbenzene, hexynenitrile and cyclohexenylacetylene.

Any known palladium complex catalyst may be used for the purpose of the present invention. Low valency complexes inclusive of zero-valent complexes may be suitably used. In this case, a precursor substance which can form in situ a low valency palladium complex during the reaction of the acetylene compound with the secondary phosphite may also be suitably used. Examples of the ligands of the palladium complex catalysts include triphenylphosphine, diphenylmethylphosphine, phenyldimethylphosphine, 1,4-bis(diphenylphosphino)butane, trimethylphosphite and triphenylphosphite. Illustrative of suitable palladium complex catalysts are bis(dibenzylideneacetone)palladium, palladium acetate, dimethylbis(triphenylphosphine)palladium, dimethylbis(diphenylmethylphosphine)palladium, ethylenebis(triphenylphosphine)palladium and tetrakis(triphenylphosphine)palladium.

The palladium complex catalyst is used in a catalytically effective amount and, generally, in an amount of up to 20 mole % based on the acetylene compound. The acetylene compound and the secondary phosphite are generally used in a stoichiometric amount. However, the use of the acetylene compound or the secondary phosphite in a stoichiometrically excess amount does not adversely affect the desired reaction.

The reaction may be carried out with or without using a solvent. The solvent, when used, may be a hydrocarbon solvent or an ether solvent. The reaction is generally performed from room temperature to about 200° C., preferably 50°–150° C. It is preferred that the reaction be carried out in an oxygen-free atmosphere, such as in the atmosphere of nitrogen, argon, methane or ethylene.

After the termination of the reaction, the product can be separated by any known manner such as chromatography, distillation and recrystallization.

The following examples will further illustrate the present invention.

EXAMPLE 1

To 1 ml of tetrahydrofuran were added 1 mmol of 1-octyne, 1 mmol of diethylphosphite and 3 mol % of cis-PdMe$_2$ (PPh$_3$)$_2$ (dimethylbis(triphenylphosphine) palladium) and the mixture was reacted at 67° C. for 5 hours in the atmosphere of nitrogen. The reaction mixture was distilled to obtain an isomeric mixture of diethyl 1-octen-2-yl-phosphonate and diethyl 1-octen-1-yl-phosphonate with a yield of 93 %. The gas chromatographic analysis revealed that the weight ratio of the former phosphonate to the latter phosphonate was 90:10.

EXAMPLES 2–7

Example 1 was repeated in the same manner as described except that the catalyst shown in Table 1 was substituted for the cis-PdMe$_2$(PPh$_3$)$_2$ catalyst, that the reaction time was increased as shown in Table 1 and that the amount of each of the 1-octyne and the diethylphosphite was decreased to 0.2M in the case of Examples 2–5 and 7. The yield of the isomeric mixture and the weight ratio of diethyl 1-octen-2-yl-phosphonate to diethyl 1-octen-1-yl-phosphonate are summarized in Table 1 together with those of Example 1.

TABLE 1

| Example No. *1 | Catalyst | Reaction Time (hr) | Yield (%) (weight ratio) |
|---|---|---|---|
| 1*2 | cis-PdMe$_2$(PPh$_3$)$_2$ | 5 | 93 (90:10) |
| 2 | cis-PdMe$_2$(PPh$_3$)$_2$ | 17 | 73 (85:15) |
| 3 | cis-PdMe$_2$(PPh$_2$Me)$_2$ | 13 | 92 (89:11) |
| 4*3 | Pd(CH$_2$=CH$_2$) (PPh$_3$)$_2$ | 6 | 93 (91:9) |
| 5 | Pd(PPh$_3$)$_4$ | 18 | 89 (86:14) |
| 6*2 | Pd(PPh$_3$)$_4$ | 22 | 69 (84:16) |
| 7 | Pd(OAc)$_2$/PPh$_3$ (1/2) | 18 | 54 (90:10) |

*1: Concentrations of 1-octyne and diethylphosphite were 0.2 M unless otherwise noted.
*2: Concentrations of 1-octyne and diethylphosphite were 1 M.
*3: Reaction was performed in the atmosphere of ethylene.

EXAMPLES 8–14

Example 3 was repeated in the same manner as described except that diethylphosphite was substituted by dimethylphosphite and that 1-octyne was substituted by hexynenitrile (Example 9), 1,8-nonadiyne (Example 10), cyclohexenylacetylene (Example 11), phenylacetylene (Example 12), p-tolylacetylene (Example 13) or diethynylbenzene (Example 14), thereby obtaining phosphonic esters. The main products are shown in Table 2. A small amount (less than 8% by weight) of an isomer of the main product was also found to be produced in each of Examples 8–14. The yields of the phosphonic esters inclusive of their isomers are also shown in Table 2.

TABLE 2

| Example No. | Acetylene compound | Product | Yield (%) |
|---|---|---|---|
| 8 | n-C$_6$H$_{13}$—≡ | 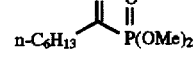 | 95 |
| 9 | NC\\\\\\≡ | 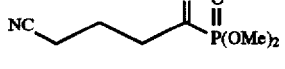 | 94 |
| 10 | ≡—(CH$_2$)$_5$—≡ | 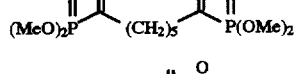 | 83 |
| 11 | 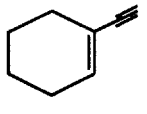 | 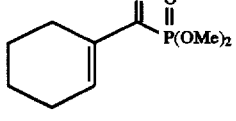 | 89 |
| 12 | Ph—≡ | 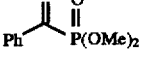 | 93 |
| 13 | 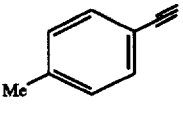 | 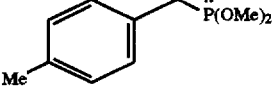 | 90 |

TABLE 2-continued

| Example No. | Acetylene compound | Product | Yield (%) |
|---|---|---|---|
| 14 | 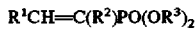 | 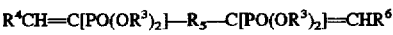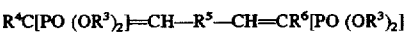 | 87 |

EXAMPLE 15

Example 1 was repeated in the same manner as described except that 4-octyne was substituted for 1-octyne and that the reaction was performed for 65 hours. Diethyl 1-propylpenten-1-yl-phosphonate was obtained with a yield of 82%.

EXAMPLE 16

EXAMPLE 8 was repeated in the same manner as described except that trimethylsilylacetylene was substituted for 1-octyne. Dimethyl 2-(trimethylsilyl)ethenylphosphonate was obtained with a yield of 41%.

EXAMPLE 17

Example 1 was repeated in the same manner as described except that 1-octyne was not used at all and that the reaction was performed in the atmosphere of acetylene gas. Dimethyl ethenylphosphonate was obtained with a yield of 20%.

EXAMPLE 18

Example 12 was repeated in the same manner as described except that 2-thienylacetylene was substituted for phenylacetylene. Dimethyl 2-(2-thienyl)vinylphosphonate was obtained with a yield of 88%.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A process for the production of an unsaturated phosphonic ester expressed by the following formula:

$$R^1CH=C(R^2)PO(OR^3)_2$$

wherein $R^1$ and $R^2$ are independently selected from the group consisting of a hydrogen atom, an alkyl group, a cycloalkyl group, an aryl group, a heteroaryl group, an aralkyl group, an alkenyl group, an alkoxy group, an aryloxy group and a silyl group and $R^3$ is selected from the group consisting of an alkyl group, a cycloalkyl group, an aralkyl group and an aryl group, said process comprising reacting an acetylene compound expressed by the following formula:

$$R^1C\equiv CR^2$$

wherein $R^1$ and $R^2$ are as defined above, with a secondary phosphite expressed by the following formula:

$$HPO(OR^3)_2$$

wherein $R^3$ is as defined above, in the presence of a palladium complex catalyst.

2. A process for the production of an unsaturated phosphonic ester expressed by at least one of the following formulas:

$$R^4CH=C[PO(OR^3)_2]—R_5—C[PO(OR^3)_2]=CHR^6$$

$$R^4C[PO(OR^3)_2]=CH—R^5—CH=CR^6[PO(OR^3)_2]$$

wherein $R^3$ is selected from the group consisting of an alkyl group, a cycloalkyl group, an aralkyl group and an aryl group, $R^4$ and $R^6$ are independently selected from the group consisting of a hydrogen atom, an alkyl group, a cycloalkyl group, an aryl group, a heteroaryl group, an aralkyl group, an alkenyl group, an alkoxy group, an aryloxy group and a silyl group and $R^5$ is a divalent group selected from the group consisting of an alkylene group, a cycloalkylene group, an arylene group, a heteroarylene group, an aralkylene group, an alkenylene group, an alkylenedioxy group, an arylenedioxy group, an oxaalkylene group and an oxaalkylenearylene group, said process comprising reacting an acetylene compound expressed by the following formula:

$$R^4C\equiv C—R^5—C\equiv CR^6$$

wherein $R^4$, $R^5$ and $R^6$ are as defined above, with a secondary phosphite expressed by the following formula:

$$HPO(OR^3)_2$$

wherein $R^3$ is as defined above, in the presence of a palladium complex catalyst.

* * * * *

UNITED STATES PATENT AND TRADEMARK OFFICE
CERTIFICATE OF CORRECTION

PATENT NO. : 5,693,826
DATED : December 2, 1997
INVENTOR(S) : TANAKA et al

It is certified that error appears in the above-indentified patent and that said Letters Patent is hereby corrected as shown below:

Col. 6, lines 17-19, "$R^1C=CR^2$" should read --$R^1C\equiv CR^2$--; and
line 30, "$R_5$" should read --$R^5$--.

Signed and Sealed this

Thirteenth Day of October 1998

*Attest:*

BRUCE LEHMAN

*Attesting Officer*     *Commissioner of Patents and Trademarks*